United States Patent [19]

Brenner et al.

[11] Patent Number: 6,063,590
[45] Date of Patent: May 16, 2000

[54] **MEMBRANE FILTER AGAR MEDIUM CONTAINING TWO ENZYME SUBSTRATES USED FOR THE SIMULTANEOUS DETECTION OF TOTAL COLIFORMS AND *E. COLI*.**

[75] Inventors: Kristen P. Brenner, Cincinnati; Clifford C. Rankin, Dayton, both of Ohio; Yvette R. Roybal, Lakewood, Colo.; Alfred P. Dufour, Cincinnatti, Ohio

[73] Assignee: The United States of America as represented by the Administrator of the U.S. Environmental Protection Agency, Washington, D.C.

[21] Appl. No.: 08/117,342

[22] Filed: Sep. 7, 1993

Related U.S. Application Data

[63] Continuation of application No. 07/793,881, Nov. 18, 1991, abandoned.

[51] Int. Cl.[7] .............................. C12Q 1/02; C12Q 1/00; C12Q 1/04; C12Q 1/10
[52] U.S. Cl. ................... 435/29; 435/4; 435/34; 435/38; 436/172
[58] Field of Search ............................ 435/4, 7.32, 7.37, 435/29, 34, 38, 968, 848, 849, 252.33; 436/172

[56] References Cited

U.S. PATENT DOCUMENTS

| | | | |
|---|---|---|---|
| 4,263,280 | 4/1981 | Kradolfer et al. | 424/114 |
| 4,714,675 | 12/1987 | Miyashita et al. | 435/32 |
| 4,923,804 | 5/1990 | Ley et al. | 435/38 |
| 4,925,789 | 5/1990 | Edberg | 435/38 |
| 5,073,488 | 12/1991 | Matner et al. | 435/31 |
| 5,210,022 | 5/1993 | Roth et al. | 435/34 |

OTHER PUBLICATIONS

Jacoby et al. Cell Cycle–Independent Lysis of *Escherichia coli* by Cefsulodin, and Inhibitor of Penicillin–Binding Proteins 1a and 1b. J. Bacteriol. 173 (1): 1–5, Jan. 1991.

Menafi, et al., *Central Journal of Hygiene* vol. 189: pp. 225–234 (1989) (Translation).

Manafi et al "A Combined Chromogenic–Fluorogenic Medium for the Simultaneous Detection of Total Coliforms & *E. Coli* in Water" Zen.Hyg.UnWelt. 189(3) 225–234 1989 Translated.

Edberg, et al. Applied & Env. Microbiology v. 54 n. 6. pp. 1595–1601 (1988).

Manafi, et al. Zbl. Hyg. 189, 225–234 (1989).

Covert et al Applied & Env Microbiology Oct. 1989 pp. 2443–2447 vol. 55 No. 10.

*Primary Examiner*—Nancy Degen
*Attorney, Agent, or Firm*—Glenna Hendricks

[57] ABSTRACT

An improved method for detection of total coliforms and *E. coli* comprising placing the target sample in a broth containing an ingredient that will encourage growth and repair of injured coliforms, at least one agent that suppresses growth of gram positive cocci and spore-forming organisms, at least one active agent that will suppress growth of non-coliform gram negative bacteria, and at least one chromogen or fluorogen has been used effectively and is cost effective. In the preferred embodiment, both a fluorogen and chromogen were used. Preferred methods include use of filter and/or plates containing the growth-promoting ingredients and the indicators.

16 Claims, No Drawings

MEMBRANE FILTER AGAR MEDIUM CONTAINING TWO ENZYME SUBSTRATES USED FOR THE SIMULTANEOUS DETECTION OF TOTAL COLIFORMS AND E. COLI.

This application is a continuation of application Ser. No. 07/793,881 filed Nov. 18, 1991 now abandoned.

FIELD OF THE INVENTION

This invention is related to means for simultaneous detection of total coliform bacteria and E. coli. The medium is particularly useful for routine testing of drinking water. A preferred medium of the invention contains a 4-methylumbelliferyl-β-D-galactopyranoside (MUGal) and indoxyl-β-D-glucuronide (IBDG) as indicators of the total coliforms (TC) and E. coli, respectively.

BACKGROUND OF THE INVENTION

The testing of water in certified laboratories for both total coliforms (TC) and E. coli at present is usually accomplished using two different tests. Testing of water for drinking and recreation use requires much time. Other samples that are frequently tested for TC and/or E. coli include urine samples (human and veterinary), foods, drugs, and pharmaceuticals. Testing of aerosols, soil and sludge are sometimes required to evaluate the need for control of harmful organisms.

Recent drinking water regulations under the Final Coliform Rule require that TC-positive drinking water samples be examined for the presence of E. coli or fecal coliforms. Use of current membrane filter technology to detect total and fecal coliforms necessitates concurrent or serial analyses using two different types of media incubated at two different temperatures. The newly promulgated prior art E. coli testing methods are confirmatory tests, not primary isolation procedures. The combined procedures (total coliform test and either fecal coliform test or E. coli method) take 28 to 48 hours. The Most Probable Number technology can take up to 72 hours.

Currently, there is no single standard method either in general usage or by approval of the U.S. Environmental Protection Agency that can detect total coliforms and E. coli simultaneously in water.

The media available present several deficiencies. Most, as previously mentioned, detect only one organism or group of organisms, and so require the use of two different tests. For example, they may test for either fecal coliforms or total coliforms or for E. coli. The use of two media analyzed either concurrently or serially will require many resources in time, labor, materials, equipment, and laboratory space. Many methods now used require one specific enzyme substrate to identify one target organism or group and use methods without enzymatic substrate for another group. Hence, two set-ups and types of media are required to meet the requirements of the regulations.

Many of the methods presently employed do not use isolation media. (They do not result in isolation of organisms directly from the sample.) Such tests are used to confirm the identity of organisms isolated on another medium. The over-all result is delay while two-step processes are accomplished to evaluate the extent of contamination.

Several tests use liquid media in a Most Probable Number (MPN) test format that permits the statistical estimation, but not enumeration, of the target organisms. Although the regulations only require the detection of the presence or absence of organisms, enumeration is useful in determining the extent of contamination and in monitoring remediation. The MPN procedure has a built-in positive bias and tends to overestimate the numbers of organisms present. This bias may result in apparent increased compliance violations and rejection of acceptable drinking water.

Many tests use ingredients that are insufficiently effective in recovering the target organisms. Failure of recovery may also result from use of elevated incubation temperatures required by some testing protocols. Elevated temperatures can result in retardation of growth or prevention of the recovery of injured organisms in the sample.

In many instances, the media are useful only for a limited range of samples. For example, it may be necessary to have a different medium for urine specimens than that for water, and a third medium may be needed to test food.

Two commercially available liquid MPN media are available in tests called Colilert and Coliquik. It is stated that both total coliforms and E. coli are detected by these tests simultaneously within 24 to 28 hours. Both utilize 2-nitrophenyl-β-D-galactopyranoside (ONPG) and 4-methylumbelliferyl-β-D-glucuronide as substrates to test for β-galactosidase and β-glucuronidase, respectively. These media are expensive. The tests result in an estimate of numbers of organisms rather than in an enumeration of target organisms. Colilert has been approved by the USEPA for total coliform analysis, but Coliquik has not, and neither test has been approved for E. coli detection. In addition, concern about the high false negative rate of Colilert with disinfected drinking water has been raised by Clark, et. al. (Clark, et. al., Abstract, *Annu. Meet. Am. Soc. Microbiol.* (1990) Q8, p. 289).

The following definitions are used in relation to substrates for detection of organisms:

A chromogen (or chromogenic substrate) is a substance, (usually colorless) that is acted upon by an enzyme to produce a pigment or dye.

A chromophore is a group on or part of a chromogen that produces a color when the chromogen is cleaved by an enzyme.

A fluorogen (or fluorogenic substrate) is a non-fluorescent material that is acted upon by an enzyme to produce a fluorescent compound.

A fluorophore is a group on or part of a fluorogen that is responsible for the fluorescence when a fluorogen is cleaved by an enzyme.

U.S. Pat. No. 4,923,804 to Ley, et al., teaches use of β-glucuronides to test for E. coli and that the indoxyl glucuronide is a preferred agent. (See Ex. 2.) However, he teaches, at column 1, 1. 50–68 that the use of MUG compounds to test for E. coli on a membrane filter test is not appropriate since the fluorescent light can be subject to interference in a membrane filter test. Hence, the teaching of Ley would discourage one from use of an agent having a 4-methylumbelliferyl fluorescent moiety in a membrane filter test. The medium differs from the substrate of the invention in several respects, 1) The medium of Ley can only detect E. coli and does not provide for detection of total coliforms. Because of this, a second medium would be required to identify total coliforms, thereby increasing the time, labor, material, and cost to the laboratory performing the analysis. 2) The base medium of Ley contains glycerol as a nutrient and lacks an inducer and an inhibitor of gram negative bacteria that can give a false positive response. Glycerol in media also causes spreading of colonies making enumeration and discrimination difficult. 3) The medium of Ley is incubated at an elevated temperature (44.5° C.) that would be detrimental to the recovery of injured microorganisms.

U.S. Pat. No. 4,591,554 to Koumura, et al., discloses use of fluorescence analysis using umbelliferone derivatives, including phosphates and galactosides. That reference also teaches use of the lactose as an inducer. The organisms are first inoculated into broth for growth. There is no inhibitor in the media, and the reference indicates, at column 3, lines 40–45 that the test also picks up Erwinia, Proteus, and Salmonella—gram negative organisms not usually classified among the coliform bacteria. The media recommended by Koumura can also promote the growth of many other types of organisms such as gram positive bacteria, yeasts and fungi that may also be present in the samples. (See Table 2 of that reference.) Some of the non-coliform organisms are able to inhibit the growth of coliforms. Hence, the tests of Koumura are not appropriate for use wherein there is a desire to find the total coliform populations.

Babelona, et al., (*J. Micro. Meth.* 12: 235–245) discloses use of MU-glucuronide complexes in testing for *E. coli* as does much of the prior art. There is no test using a non-fluorescing chromogen-glucuronide to test for *E. coli,* nor is there any MU-galactoside test for total coliforms.

An agar medium developed by Petzel and Hartman (*Appl. Environ. Microbiology,* Vol 24: 925–933) used a selective medium for total coliform identification combined with detection of *E. coli* using 4-methylumbelliferyl-β-D glucuronide. Problems with this medium include the inability to use standard diluents, a high false positive rate when high levels of Flavobacterium species or oxidase positive organisms were present in the water samples, and difficulty distinguishing the natural fluorescence of Pseudomonads from the fluorescence produced during substrate breakdown. Furthermore, this medium could not be used for precise enumeration of the target organisms because of the large number of other Gram negative bacteria that grew on it.

An agar medium using two different enzyme substrates and a different base medium than those used in the MUGal-IBDG Agar of the invention was recently developed in Germany to simultaneously detect both total coliforms and *E. coli.* Total coliform colonies were identified by the production of blue color from the β-galactosidase cleavage of the substrate X-gal (5-bromo-4-chloro-3-indolyl-β-D-galactopyranoside), while *E. coli* colonies were detected by the fluorescence of 4-methylumbelliferone, produced by the cleavage of 4-methylumbelliferyl-β-D-glucuronide by β-glucuronidase (Manafi and Kneifel, *Zbl. Hyq.* 189: 225–234). The reference teaches the use of broth or agar containing 4-methylumbelliferyl-β-D-glucuronide (MUG) and a galactoside with a non-fluorescing chromophore (X-Gal). It also teaches a 4-methylumbelliferyl-β-D-galactoside (MUGal) with a glucuronide attached to a non-fluorescing chromophore, 4-nitrophenyl-β-D-glucuronide (PNPG), in an agar medium containing bile salts to inhibit the growth of organisms that are not coliform bacteria. It is reported that the results of use of this media to test drinking water were not good (p. 230). Manafi attributes his difficulties to the color of the drinking water and the reagent. Manafi indicates that effectiveness of reagents on solid and liquid media differs.

Manafi, et al., *Microbiological Rev.* 55: 335–348 (1991), is a general review article about fluorogenic and chromogenic substrates used in bacterial diagnostics. The particular preferred fluorogenic and chromogenic agents and nutrient substrates used in the invention are not taught therein, and no guidance is provided therein regarding use of inhibitors as required by the instant invention.

DESCRIPTION OF THE INVENTION

It is the purpose of this invention to provide a bacterial growth medium that will support repair and growth of total coliform bacteria, including *E. coli,* while suppressing the growth of gram possitive cocci and spore-forming organisms and gram negative organisms that would give a false positive reading. The media of the invention may also contain an inducer.

It is a further object of the invention to provide a means of detecting and enumerating both total coliforms (TC) and *E. coli* simultaneously. The method of the invention simplifies compliance with the Final Coliform Rule of EPA and prevents rejection of acceptable drinking water that may occur due to the recovery of thermotolerant species other than *E. coli* with fecal coliform media. Only one incubator is needed (35° C.), and the 35° C. incubation temperature permits the growth of both types of target organisms with the maximum recovery of injured organisms. The method of the invention is both sensitive and specific. False positive and negative rates for *Escherichia coli* are lower than results on other media. Flavobacterium species and Aeromonas, typical false positive organisms on other coliform media, are inhibited. This method recovers significantly more total coliforms and *E. coli* than other media tested (mEndo, mTEC). It can be used to show only the presence or absence of Total Coliforms and *Escherichia coli,* if desired.

The preferred embodiment of the invention uses familiar membrane filter technology. The media of the invention are less expensive than Colilert or Coliquik and will be even less expensive when widely used. The media of the invention are useful with several types of water and may be used with other types of samples as well. It is possible to use other media disclosed herein for other applications to detect TC and/or *E. coli.*

EXAMPLE

Medium Formulation

This medium incorporates two different enzyme substrates to simultaneously identify two different types of bacteria (total coliforms and *E. coli*) by means of their specific enzyme reactions in a selective base agar that favors the growth of Gram negative organisms in general and that of coliforms and *E. coli* in particular. The agar medium has the following formulation in grams/liter:

| Ingredient | Amount (g/l) |
|---|---|
| Proteose Peptone #3 | 5.0 |
| Yeast Extract | 3.0 |
| β-D-Lactose | 1.0 |
| 4-Methylumbelliferyl-β-D-Galactopyranoside (MUGal) (final concentration 100 μg/ml) | 0.1 |
| NaCl | 7.5 |
| $K_2HPO_4$ | 3.3 |
| $KH_2PO_4$ | 1.0 |
| Sodium Lauryl Sulfate | 0.2 |
| Sodium Desoxycholate | 0.1 |
| Agar | 15.0 |
| Distilled Water | 1000 milliliters |

The medium was autoclaved for 15 minutes at 121° C., and 20 ml of a freshly-prepared 16 mg/ml sterile-filtered solution of Indoxyl-β-D-Glucuronide (IBDG) (320 μg/ml final concentration) and 5 ml of a freshly-prepared 1 mg/ml sterile-filtered solution of Cefsulodin (5 µg/ml final concentration) were added per liter of tempered agar medium. The medium was pipetted into 9×50 mm Petri dishes (5 ml/plate).

The substrate MUGal was used to identify total coliforms. These organisms produce the enzyme β-Galactosidase which cleaves the MUGal to produce 4-Methylumbelliferone, a compound that makes the bacterial colonies or growth fluoresce bluish white when exposed to long wave ultraviolet light (λ=366 nm). Non-coliform colonies do not fluoresce. The substrate IBDG was included to detect the growth of *E. coli*. These organisms produce the enzyme β-Glucuronidase which cleaves the substrate to form a blue color (indigo) in the colonies or growth. Since *E. coli* is also a total coliform and hence, produces β-galactosidase, the blue colonies fluoresce (blue-green) under long wave ultraviolet light. Organisms other than *E. coli* do not generally produce the blue color.

Proteose peptone #3 and yeast extract, common medium ingredients, were added to encourage the growth of the bacteria and the repair of injured organisms. Agar acted as a solidifying agent in the medium. Sodium lauryl sulfate and sodium desoxycholate were used to inhibit Gram positive cocci and spore-forming organisms, but not the Gram negative enteric bacteria (e.g., coliforms and *E. coli*). The salts (NaCl, $K_2HPO_4$ and $KH_2PO_4$) were used as nutrients and helped to maintain a neutral pH, thereby preventing the detrimental accumulation of acid from the breakdown of lactose and other nutrients. A small amount of β-D-lactose was added as a general nutrient and to induce β-galactosidase production by the total coliforms.

The antibiotic Cefsulodin was used to inhibit Gram positive bacteria and some non-coliform Gram negative organisms that can cause false positive reactions.

Results

Test Procedure

One-milliliter or larger volumes of samples or their dilutions, prepared in phosphate-buffered dilution water, or dilutions of bacterial cultures, were filtered through 0.45 µm pore size cellulose ester membrane filters, and the filters were aseptically placed on the surface of the agar plates. The plates were incubated at 35° C. for 16–24 hours, and the colonies that grew were inspected for blue color (i.e., production of indigo from IBDG by the *E. coli* enzyme β-glucuronidase), fluorescence under long wave ultraviolet light (i.e., production of 4-Methylumbelliferone from MUGal by the total coliform enzyme β-galactosidase), or both. For optimal differentiation of fluorescent and non-fluorescent colonies, the ultraviolet lamp was held at a distance of about 6" from the plates. Counts were made of the total coliforms and *E. coli* found. In some instances, only the presence or absence of each was noted.

Although most *E. coli* can grow at elevated temperatures (40–45° C.), many other coliforms cannot. Therefore, the medium should be incubated at 35–37° C. for 16–24 hours for maximum growth of both organisms. (Growth can also occur at temperatures as low as 20° C., though much more slowly.) Although only 100 µg/ml MUGal and 320 µg/ml IBDG are recommended because of cost, larger amounts of MUGal (e.g., 200 µg/ml) and IBDG will also work satisfactorily. IBDG can be autoclaved in the medium. Other forms of MUGal and/or IBDG (e.g., the cyclohexylammonium salt of IBDG) or compounds producing the same or a substituted final product (e.g., a 5-Bromo-4-Chloro-3-Indolyl-β-D-Glucuronic acid salt (for example, sodium or cyclohexylammonium salts), commonly referred to as X-GLUC) can be used in similar or different amounts. Different β-galactosidase substrates (e.g., Chlorophenol Red-β-D-Galactopyranoside or Resorufin-β-D-Galactopyranoside) or β-glucuronidase substrates can be used successfully in this base medium, but the concentrations must be adjusted for each compound. Filters of other compositions (e.g., cellulose nitrate) and other pore sizes from 0.22–0.8 µm will also work in this method.

To illustrate the specificity and selectivity of MUGal-IBDG Agar for total coliforms and *E. coli*, two sets of analyses were performed. First, dilutions of known bacterial cultures were filtered using the test procedure described above, and the filters were placed on plates of MUGal-IBDG Agar. After incubation at 35° C. for 16–24 hours, the plates were observed for blue color, fluorescence, or both. The results are shown in Table 1.

In the second test, a series of natural water samples (chlorinated drinking water, groundwater, effluent, and surface water) were filtered, and colonies of each type (blue, fluorescent; non-blue, fluorescent; non-blue, non-fluorescent; blue, non-fluorescent) were counted. Some of each type were picked from MUGal-IBDG Agar for identification using API 20E strips. Similar volumes of each sample were filtered, and the filters were placed on coliform (mEndo Agar) and *E. coli* (mTEC Agar) comparison media. After incubation of the media at their appropriate times and temperatures, target and non-target/background colonies were counted and compared with the corresponding counts on MuGal-IBDG Agar. The formula of the example was designated "MI" medium.

Results of the recovery study showed that the new medium recovered significantly more total coliforms and *E. coli* than the comparison media, and that the number of background colonies on MUGal-IBDG Agar was significantly less than the corresponding values on the other media. Of the blue colonies picked for identification, 95.7% (66/69) were *E. coli*, and 91.3% (95/104) of the fluorescent, non-blue colonies were total coliforms. In addition, 93.8% (61/65) of the background (non-blue, non-fluorescent) colonies were found to be non-coliforms. The reactions of some representative isolates from the natural water samples are shown in Table 2.

TABLE 1

REACTIONS OF SEVERAL BACTERIA ON MUGAL-IBDG AGAR

| Test Organism | Reactions on MUGal-IBDG Agar: | |
|---|---|---|
| | Blue Color (β-Gluc[1]) | Fluorescence (β-Gal[2]) |
| *Escherichia coli* (EPA 206) | + | + |
| *Escherichia coli* (ATCC 25922) | + | + |
| *Enterobacter aerogenes* (EPA 202) | − | + |
| *Klebsiella pneumoniae* (EPA 207) | − | + |
| *Citrobacter freundii* (ATCC 8090) | − | + |
| *Pseudomonas aeruginosa* (ATCC 27853) | − | − |

[1]β-Gluc, β-Glucuronidase activity.
[2]β-Gal, β-Galactosidase activity.

TABLE 2

REACTIONS OF SEVERAL BACTERIAL ISOLATES ON MUGAL-IBDG AGAR

| Organism Identified | Reactions on MUGal-IBDG Agar: | |
|---|---|---|
| | Blue Color (β-Gluc[1]) | Fluorescence (β-Gal[2]) |
| *Escherichia coli* | + | + |
| *Klebsiella pneumoniae* | − | + |
| *Klebsiella ozonae* | − | + |
| *Klebsiella oxytoca* | − | + |
| *Citrobacter freundii* | − | + |
| *Citrobacter amalonaticus* | − | + |
| *Enterobacter cloacae* | − | + |
| *Enterobacter aerogenes* | − | + |
| *Enterobacter agglomerans* | − | + |
| *Pseudomonas aeruginosa* | − | − |
| Salmonella species | − | − |
| *Aeromonas hydrophila* | − | − |
| *Yersinia enterocolitica* | − | − |
| Achromobacter species | − | − |
| *Acinetobacter calco. var lwoffi* | − | − |

[1] β-Gluc, β-Glucuronidase activity.
[2] β-Gal, β-Galactosidase activity.

The results from the two sets of analyses showed that the medium successfully distinguished between *E. coli*, total coliforms, and background or non-coliform organisms using the two enzyme substrates in a unique basal medium.

Various alternative methods of practicing the invention would be understood to be possible by those of skill in the art. Following are examples of possible alternative means. The media of the invention may also be used in confirmation tests wherein bacterial growth samples are taken from primary cultures grown from the test sample.

Alternative 1
MUGal-IBDG Agar in Spread, Swab, or Streak Plates

The agar medium was prepared as before, poured into 9×50 mm (5 ml/plate) or 50×100 mm (15–20 ml/plate) Petri dishes, and allowed to harden. A small quantity of bacterial culture or sample was applied to and spread on the surface of the agar plates (with or without a membrane filter) by means of an inoculating needle or loop, a cotton swab, a toothpick, a pipette, a glass hockey stick, or other means. The plates were incubated inverted at 35° C. for 8–24 hours, and the growth was observed as before for the presence of blue color and/or fluorescence under long wave ultraviolet light (366 nm). The results of spreading several cultures on this medium are shown in Table 3.

Alternative 2
MUGal-IBDG Agar as a Pour Plate

One milliliter aliquots of bacterial cultures or samples and/or dilutions of cultures or samples in phosphate-buffered dilution water were pipetted into sterile 15×100 mm Petri dishes. About 15–20 ml of the tempered agar, prepared as before, was added to each plate, and the plate was gently swirled to mix the bacteria with the agar. The plates were allowed to harden and were incubated inverted at 35° C. for 16–24 hours. Colonies were observed for the presence of blue color and/or fluorescence under long wave ultraviolet light (366 nm). The results obtained with several cultures were the same as those shown in Table 3.

TABLE 3

REACTIONS OF SEVERAL BACTERIA ON MUGAL-IBDG AGAR

| Test Organism | Reactions on MUGal-IBDG Agar: | |
|---|---|---|
| | Blue Color (β-Gluc[1]) | Fluorescence (β-Gal[2]) |
| *Escherichia coli* (EPA 206) | + | + |
| *Escherichia coli* (ATCC 25922) | + | + |
| *Enterobacter aerogenes* (EPA 202) | − | + |
| *Klebsiella pneumoniae* (EPA 207) | − | + |
| *Pseudomonas aeruginosa* (ATCC 27853) | − | − |

[1] β-Gluc, β-Glucuronidase activity.
[2] β-Gal, β-Galactosidase activity.

Alternative 3
MUGal-IBDG Agar in Slants or Stab Cultures

The agar was prepared as before, and 10 ml aliquots were pipetted into sterile screw-cap tubes. The agar was allowed to harden in the upright vertical position for stab cultures or at an angle for slant cultures. The cultures were inoculated by stabbing with an inoculating needle or streaking with a loop, swab, or other means, respectively, and observed for the typical blue color and/or fluorescence as before. The results with several bacterial cultures were the same as those shown in Table 3.

Alternative 4
MUGal-IBDG as a Liquid Medium (Without the Agar)

The liquid media exemplified below are made in the same manner as the medium of the example, except that the agar is omitted.

(4a) Use with Absorbent Pads

Aliquots of 1.8–2.0 ml of sterile broth were pipetted onto sterile absorbent pads, aseptically placed in 9×50 mm Petri dishes. Cultures or samples, or dilutions of them, were filtered through 0.45 μm pore size cellulose ester membrane filters as before, and the filters were placed on top of the pads saturated with the broth. The plates were incubated inverted for 8–24 hours, and colonies were observed for blue color and/or fluorescence, as previously described. Results with several bacterial cultures were the same as those shown in Table 3.

(4b) Most-Probable Number (MPN) Method

Single- and double-strength liquid media were prepared as in the example except that the agar was omitted and, for double-strength media, all amounts except the water were doubled. The media were pipetted into sterile tubes in 10 ml volumes. Ten-milliliter volumes of a drinking water sample were inoculated into 10 tubes of double-strength medium. The tubes were incubated for 16–24 hours, and observed for blue-green color and/or precipitate (indicating the presence of *E. coli*) and/or fluorescence under long wave ultraviolet light (366 nm) (indicating the presence of total coliforms). A tube of uninoculated medium (negative control) was also incubated and used as a comparator tube to identify the positive and negative tubes. Other types of samples were analyzed using this method or the standard 5-tube, 3-dilution (or amount) MPN format. In the latter method, each of three different amounts or dilutions of sample were inoculated into five tubes. Volumes of 10 ml were pipetted into double-strength medium tubes, and 1 ml volumes of samples, cultures, or their dilutions were placed in tubes of single-strength medium. The 15-tube test was incubated and observed as before. In either format, the numbers of positive tubes for each type of organism (i.e., *E. coli* or total coliforms) were counted for each dilution or volume and compared with standard 5- or 10-tube MPN tables to determine the estimated number of organisms per 100 ml sample.

(4c) Microtiter Confirmation/Identification Test

The liquid medium was prepared as before, and aliquots were pipetted into each well of a sterile microtiter plate (2 ml into each well of the 24 well plate or 200 μl into each well of a 96-well microtiter plate). The plates were inoculated with bacterial strains to be tested and incubated at 35° C. for up to 24 hours. The wells were observed for blue-green color and/or fluorescence under long wave ultraviolet light (366 nm). The results with several bacterial strains were similar to those shown in Table 3. Natural samples can also be analyzed for presence or absence of *E. coli* and/or total coliforms using this method, and the procedure can be automated.

(4d) Confirmatory Tube Test

The liquid medium was prepared as described above, and 10 ml volumes were aseptically pipetted into sterile screw-cap tubes. Bacterial cultures or small amounts of growth from a slant, stab, or isolated colony were inoculated into the media tubes. After incubation at 35° C. for up to 24 hours, the tubes were observed for the blue-green color and/or fluorescence under long wave ultraviolet light. The color reactions with the same five cultures used before were similar to those shown in Table 3.

Alternative 5

Use of the Enzymes Substrates in a Confirmatory Spot Test for Total Coliforms and *E. coli*

One hundred microliter volumes of a bacterial suspension were placed in three wells of a sterile porcelain spot test plate or other suitable plate with wells. The bacterial suspension was obtained in one of the following ways:

1. A loopful of bacterial growth from a slant or an isolated colony from an agar plate was emulsified in a small amount of the liquid medium without substrates or other non-selective broths.
2. Aliquots of 100 μl of a bacterial culture grown overnight at 35° C. in a non-selective broth or the liquid medium without substrates were used.

Sixty microliters of a freshly-prepared, filter-sterilized 16 mg/ml IBDG solution was added to one well of bacterial suspension, and 300 μl of a freshly-prepared, filter-sterilized 1 mg/ml MUGal solution was added to a second well. The third well, containing only bacterial suspension (negative control), was used as a comparator to distinguish positive and negative wells. Additional wells were inoculated with uninoculated medium, IBDG, and MUGal as controls. The plates were covered with sterile foil and incubated at 35° C. for up to 24 hours. Wells were observed for blue color or fluoresence under long wave ultraviolet light (366 nm) at hourly intervals, as positive reactions have been observed within a few hours. Results of spot tests with several cultures are shown in Table 4.

TABLE 4

COLOR REACTIONS OF SEVERAL BACTERIA IN THE SPOT TEST

| Test ORGANISM | Reactions in Wells Containing: | | |
|---|---|---|---|
| | IBDG[1] | MUGal[2] | No IBDG NO MUGal[3] |
| *Escherichia coli* (EPA 206) | + | + | -/- |
| *Escherichia coli* (ATCC 25922) | + | + | -/- |
| *Enterobacter aerogenes* (EPA 202) | - | + | -/- |
| *Klebsiella pneumoniae* (EPA 207) | - | + | -/- |
| *Pseudomonas aeruginosa* (ATCC 27853) | - | - | -/- |
| Medium only[4] (No bacteria) | - | - | -/- |

[1] A positive reaction is shown by production of a blue color in the well.
[2] A positive reaction is shown by fluorescence of the well under long wave ultraviolet light.
[3] Negative controls and comparator wells. The two negatives indicate no blue color and no fluorescence in the wells.
[4] Reagent and medium controls.

Note: The other temperatures, amounts, etc., described in the example of the preferred embodiment also apply to the alternate embodiments.

The selective base medium without the substrates MUGal and IBDG (with or without agar) can be used with other β-galactosidase and β-glucuronidase substrates for the detection of total coliforms and/or *E. coli*. For example, each of three other β-galactosidase substrates (2-Nitrophenyl-β-D-galactopyranoside, Chlorophenol Red-β-galactopyranoside, and Resorufin-β-D-Galactopyranoside) have been tested with IBDG in this lab. The colors of the total coliform colonies were yellow, orchid, and pink-red, respectively, and the *E. coli* colonies were varying shades of blue. We believe other combinations of substrates in this base medium would also work in the various embodiments described in this document, and different enzyme substrates (other than β-galactosidase and β-glucuronidase substrates) for specific coliforms could be used in this base medium because of its selectivity. The following guidance is provided for choosing ingredients for the alternative embodiments.

Two chromogenic and/or fluorogenic enzyme substrates are needed in this selective base medium: one is a Beta-D-galactoside (or Beta-D-galactopyranoside) with an attached chromophore or fluorophore that is specifically cleaved by the enzyme Beta-D-galactosidase, produced by total coliform bacteria, and the other is a Beta-D-glucuronide (or Beta-D-glucuronic acid) with an attached chromophore or fluorophore that is specifically cleaved by the enzyme Beta-glucuronidase, produced by *Escherichia coli*. The two substrates should be colorless or non-fluorescent until cleaved by their specific enzyme. Two chromogens, two fluorogens, or a chromogen and a fluorogen may be used if the criteria listed below are met. The chromogens or fluorogens produced after enzyme cleavage should be in a form that is usable to the target microorganisms.

If two chromogens are used, two different contrasting-color chromophores should be produced upon specific enzyme cleavage, and a third distinct color should be produced by the presence of both colors in the colonies of organisms that have both enzymes. All three colors should be easily distinguished from one another. Both substrates should remain colorless until cleaved by their specific enzymes and should not spontaneously breakdown in the medium.

If a chromogen and a fluorogen are used, the color or fluorescence, respectively, from one compound should not interfere with the discrimination and/or interpretation of the other. The chromogen should not exhibit non-specific or natural fluorescence under the conditions used for the fluorogen, and the fluorogen should not produce an interfering color under conditions used for the chromogen.

If two fluorogens are used, the two compounds should have considerably different excitation and emission wavelengths. In addition, organisms that produce both enzymes should be easily distinguished from those producing only one enzyme.

The substrates, separately or in combination, should not be toxic or inhibitory to either of the target microorganisms and should not encourage the growth of the non-target or background organisms. Inhibition of the non-target bacteria and/or enhancement of the growth of the target microorganisms is desirable.

Upon cleavage, chromogens should produce insoluble or only slightly soluble chromophores that will remain localized in the bacterial colonies. Similarly, fluorophores should not diffuse away from the colonies, as excessive diffusion hinders target colony recognition, discrimination, and enumeration.

It is necessary that the chromogens and/or fluorogens be water-soluble and/or be able to withstand autoclaving without breaking down. In addition, the substrates should be stable in the medium and should not interact with or be detrimentally affected by the other medium ingredients.

If enzymes other than Beta-D-galactosidase and Beta-D-glucuronidase are used to detect other specific coliforms in this selective base medium, the chromogen(s) and/or fluorogen(s) utilized should be specific for the enzyme(s) and should meet the other criteria listed above.

Antibiotics or chemicals other than Cefsulodin may be used as inhibitors of Gram positive and false positive, Gram negative bacteria if they are stable in the medium, do not interact detrimentally with the other medium ingredients, and are not toxic or inhibitory to either of the two target organisms.

The proteose peptone #3 and yeast extract exemplified may be replaced with other ingredients that encourage growth of bacteria and repair of injured organisms. Failure to provide for repair of injured organisms may result in false negative results.

The sodium lauryl sulfate and sodium desoxycholate may be replaced with other chemicals (including other salts) which inhibit Gram positive cocci and spore-forming organisms, but not the Gram negative enteric bacteria. However, the salts exemplified are both inexpensive and readily available and do no injure the target organisms, all important factors in choosing inhibiting chemicals for use in these media.

The buffering salts (NaCl, $K_2HPO_4$ and $KH_2PO_4$) can be replaced with other buffers if those buffers perform similarly in this medium and do not adversely affect target organism growth, recovery, and/or discrimination. However, metabolizing organisms may break down or convert some buffers to compounds that may affect the chromogenic and/or fluorogenic substrates, their chromophores or fluorophores.

The use of an inducer (β-D-lactose was exemplified) is optional. However, in media lacking the lactose the colonies were less discrete. Hence, it was felt the addition of such an inducer was advantageous.

Other Combinations of Chromogens and Fluorogens that Work in this Selective Medium 1. Red Gal and X-Gluc (Either the sodium salt or the cyclohexylammonium salt)
   Best: 200 mg/l and 50 mg/l, respectively
   Ranges: 200–800 mg/l and 25–320 mg/l, respectively
   Appearance:
     Total coliforms: dusty rose to maroon
     *E. coli:* cadet blue (grey-blue)
2. X-Gal and Red Gluc
   Best: 50 mg/l and 400 mg/l, respectively
   Ranges: 50–200 mg/l and 200–400 (or more) mg/l, respectively
   Appearance:
     Total coliforms: aquamarine/light turquoise
     *E. coli:* Dark cadet blue
3. MUGal and Red Gluc
   Best: 100 mg/l and 400 mg/l, respectively
   Ranges: 50–200 mg/l and 200–400 (or more) mg/l, respectively
   Appearance:
     Total Coliforms: blue-white fluorescense under long wave ultraviolet light (366 nm)
     *E. coli:* dusty rose (ordinary light), blue-purple fluorescence under long wave ultraviolet light.
   Note: Ordinarily the double fluorescence would be a problem, but the colors of the fluorescence are different in this instance.
4. Red Gal and IBDG (Either the sodium salt or the cyclohexylammonium salt)
   Best: 200 mg/l and 320 mg/l, respectively
   Ranges: 200–800 mg/l and 200–800 mg/l, respectively
   Appearance:
     Total coliforms: dusty rose to maroon
     *E. coli:* blue-violet
5. X-Gal and MUGluc
   Best: 50 mg/l and 100 mg/l, respectively
   Ranges: 50–200 mg/l and 50–200 mg/l, respectively
   Appearance:
     Total coliforms: aquamarine/light turquoise
     *E. coli:* blue-white halo around a dark blue center under long wave ultraviolet light (366 nm)
6. MUGal and X-Gluc
   Best: 100 mg/l and 50–100 mg/l, respectively
   Range: 50–200 mg/l and 10–320 mg/l, respectively
   Appearance:
     Total coliforms: blue-white florescence in long wave ultraviolet light (366 nm)
     *E. coli:* turquoise

| CHROMOGEN AND FLUOROGEN ABBREVIATIONS | |
| --- | --- |
| X-Gluc | 5-Bromo-4-Chloro-3-Indolyl-Beta-D-glucuronic Acid, sodium salt or cyclohexylammonium salt |
| MUGluc | 4-Methylumbelliferyl-Beta-D-glucuronide |
| Red Gal | 6-Chloro-3-Indolyl-Beta-D-galactoside |
| Red Gluc | 6-Chloro-3-Indolyl-Beta-D-glucuronic Acid, mono-cyclohexylammonium salt |
| X-Gal | 5-Bromo-4-Chloro-3-Indolyl-Beta-D-galactoside |
| IBDG | Indoxyl-Beta-D-glucuronide, sodium salt or cyclohexylammonium salt |
| MUGal | 4-Methylumbelliferyl-Beta-D-galactopyranoside |

An advantage of the method of the invention is that it is quite cost effective. For example, the cost of most agar plates is $0.03 to $0.07. The cost of the plates in using this method ranged from $0.11 to $2.46. The last is the price when using the Sigma cyclohexylammonium salt of the of IBDG. The cost of the medium containing the sodium salt of IBDG was $0.27 per plate. Although this price is slightly higher than the media currently used, only one analysis employing one medium and one incubator are required instead of the usual double testing. The use of this agar medium with two chromogens, a chromogen and a fluorogen, or two fluorogens to detect both TC and *E. coli* in one medium results in significant reduction in time, space, materials, equipment and personnel needed to perform TC and *E. coli* testing using prior methods. The savings to the laboratory far exceed the small additional cost of the plates. Furthermore, the liquid Most Probable Number (MPN) and Presence/Absence (PA) media containing chromogens and/or fluorogens (price range: $6.00 to $13.00 per test) sold as Colilert and ColiquiK are much more expensive than the media of the invention.

We claim:

1. A growth medium for detection of total coliforms and *E. coli* comprising a broth containing:
    (1) a growth-encouraging effective amount of ingredients as means of supporting growth and repair of injured coliforms,
    (2) buffers to maintain a Ph of 6.5 to 8,
    (3) at least one agent that suppresses growth of gram positive cocci and spore-forming organisms,
    (4) at least one agent to suppress growth of non-coliform gram negative bacteria, and
    (5) at least one chromogen and one fluorogen.

2. A medium of claim 1 containing, additionally, a solidifying agent.

3. A medium of claim 1 containing at least one chromophore or fluorophore attached to a galactoside or glucuronide.

4. A medium of claim 1 wherein the agent used to suppress growth of non-coliform gram negative bacteria is a cephalosporin.

5. A medium of claim 4 wherein the cephalosporin used to suppress growth of non-coliform bacteria is Cefsulodin.

6. A medium of claim 1 containing a chromophore attached to a qlucuronide or salt of glucuronic acid and a fluorophore attached to a galactoside or a chromophore attached to a galactoside and a fluorophore attached to a glucuronide or a salt of glucuronic acid.

7. A growth medium of claim 6 for simultaneous detection of total coliforms and *E. coli* comprising broth containing either (1) a 4-methylumbelliferyl-β-D-galactoside and an indoxyl-β-D glucuronide or (2) a 4-methylumbelliferyl-β-D-glucuronide and an indoxyl-β-D-galactoside.

8. A medium of claim 6 wherein the glucuronide is 4-methylumbelliferyl-β-D-glucuronide and the galactoside is 5-bromo-4-chloro-3-indolyl-β-D-galactoside.

9. A medium of claim 6 wherein the galactoside is 6-chloro-3-indolyl-β-D-galactoside and the salt of glucuronic acid is 5-bromo-4-chloro-3-indolyl-β-D-glucuronic acid, sodium or cyclohexylammonium salt.

10. A medium of claim 6 wherein the galactoside is 5-bromo-4-chloro-3-indolyl-β-D-galactoside and the salt of the glucuronic acid is 6-chloro-3-indolyl-β-D-glucuronic acid mono-cyclohexylammonium salt.

11. A medium of claim 6 wherein the galactoside is 4-methylumbelliferyl-β-D-galactopyranoside and the glucuronic acid salt is 6-chloro-3-indolyl-β-D-glucuronic acid monocyclohexylammonium salt.

12. A medium of claim 6 wherein the galactoside is 6-chloro-3-indolyl-β-D-galactoside and the glucuronide is indoxyl-β-D-glucuronide, sodium or cyclohexylammonium salt.

13. A medium of claim 6 wherein the galactoside is 4-methylumbelliferyl-β-D-galactopyranoside and the glucuronide is indoxyl-β-D-glucuronide, sodium or cyclohexylammonium salt.

14. A medium of claim 6 wherein the galactoside is 4-methylumbelliferyl-β-D-galactopyranoside and the glucuronic acid salt is 5-bromo-4-chloro-3-indolyl-β-D-glucuronic acid sodium or cyclohexylammonium salt.

15. A medium of claim 6 containing agar.

16. A growth medium for detection of total coliforms and *E. coli* comprising a broth containing:
    1) a growth encouraging effective amount of an ingredient that will encourage growth and repair of injured coliforms,
    2) buffers to maintain a pH of 6.5 to 8,
    3) at least one agent that suppresses growth of gram positive cocci and spore-forming organisms,
    4) at least one agent that will suppress growth of non-coliform gram negative bacteria, and
    5) at least one chromogen or fluorogen wherein the chromogen and/or fluorogen is not the primary source of nutrient for said organisms.

* * * * *

(12) EX PARTE REEXAMINATION CERTIFICATE (5238th)
United States Patent
Brenner et al.

(10) Number: US 6,063,590 C1
(45) Certificate Issued: Nov. 29, 2005

(54) MEMBRANE FILTER AGAR MEDIUM CONTAINING TWO ENZYME SUBSTRATES USED FOR THE SIMULTANEOUS DETECTION OF TOTAL COLIFORMS AND E. COLI

(75) Inventors: Kristen P. Brenner, Cincinnati, OH (US); Clifford C. Rankin, Dayton, OH (US); Yvette R. Roybal, Lakewood, CO (US); Alfred P. Dufour, Cincinnati, OH (US)

(73) Assignee: The United States of America as represented by the Administrator of the Environmental Protection Agency, Washington, DC (US)

Reexamination Request:
No. 90/006,387, Sep. 23, 2002

Reexamination Certificate for:
Patent No.: 6,063,590
Issued: May 16, 2000
Appl. No.: 08/117,342
Filed: Sep. 7, 1993

Related U.S. Application Data

(63) Continuation of application No. 07/793,881, filed on Nov. 18, 1991, now abandoned.

(51) Int. Cl.$^7$ ............... C12Q 1/02; C12Q 1/00; C12Q 1/04; C12Q 1/10
(52) U.S. Cl. ............... 435/29; 435/4; 435/34; 435/38; 436/172
(58) Field of Search ............... 435/4, 7.32, 7.37, 435/29, 34, 38, 252.33; 436/172

(56) References Cited

U.S. PATENT DOCUMENTS

| | | |
|---|---|---|
| 4,000,041 A | 12/1976 | Lanham et al. |
| 4,072,572 A | 2/1978 | Lanham et al. |
| 4,072,575 A | 2/1978 | Lanham et al. |
| 4,340,671 A | 7/1982 | Gibson |

OTHER PUBLICATIONS

"Membrane Filter Method for the Enumeration of Chlorine Damaged Coliforms in Drinking Water", Duncanson, Proceedings, Water Quality Technology Conference, Nov. 16–20, 1986, pp. 57–69.
"A Combined Chromogenic–Fluorogenic Medium for the Simultaneous Detection of Total Coliforms and E. coli in Water", Manafi et al., 261 Hyg 189, 225–234 (1989).
"Schnellnachweiz von Bakterien mittels fluorogener und chromogener Substrate", Manafi, Forme Stadte–Hygiene 41 (1990) Jul./Aug.: 181–184.
"Application of Chromophoric and Fluorophoric Substrates to Rapid Bacterial Identification" Manafi et al., Applied Fluorescence Technology, pp. 11–13, vol. 1, 1989.
"Nalidixic Acid as a Selective Agent for the Isolation of Enterobacteria from River Water", Hughes, J. Hyg., Camb. (1976) 77, 23.
"Membrane Filter Method for the Enumeration of Total Coliforms", Duncanson et al., Abstracts of the Annual Meeting—1983, ASM—vol. 83, Abstract Q 22.

*Primary Examiner*—James Ketter

(57) ABSTRACT

An improved method for detection of total coliforms and E. coli comprising placing the target sample in a broth containing an ingredient that will encourage growth and repair of injured coliforms, at least one agent that suppresses growth of gram positive cocci and spore-forming organisms, at least one active agent that will suppress growth of non-coliform gram negative bacteria, and at least one chromogen or fluorogen has been used effectively and is cost effective. In the preferred embodiment, both a fluorogen and chromogen were used. Preferred methods include use of filter and/or plates containing the growth-promoting ingredients and the indicators.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 4 is cancelled.

Claims 1, 5 and 16 are determined to be patentable as amended.

Claims 2, 3 and 6–15, dependent on an amended claim, are determined to be patentable.

1. A growth medium for detection of total coliforms and E. coli comprising a broth containing:
   (1) a growth-encouraging effective amount of ingredients as means of supporting growth and repair of injured coliforms,
   (2) buffers to maintain a Ph of 6.5 to 8,
   (3) at least one agent that suppresses growth of gram positive cocci and spore-forming organisms,
   (4) [at least one agent to suppress growth of non-coliform gram negative bacteria] *at least one cephalosporin*, and
   (5) at least one chromogen and one fluorogen.

5. A medium of claim [4 wherein the cephalosporin used to suppress growth of non-coliform bacteria is] *1 wherein the cephalosporin bacteria is Cefsulodin.*

16. A growth medium for detection of total coliforms and E. coli comprising a broth containing:
   1) a growth encouraging effective amount of an ingredient that will encourage growth and repair of injured coliforms,
   2) buffers to maintain a pH of 6.5 to 8,
   3) at least one agent that suppresses growth of gram positive cocci and spore-forming organisms,
   4) [at least one agent that will suppress growth of non-coliform gram negative bacteria] *at least one cephalopsorin*, and
   5) at least one chromogen or fluorogen wherein the chromogen [and/] *or* fluorogen is not the primary source of nutrient for said organisms.

* * * * *